United States Patent [19]

Ibbotson

[11] 4,007,140
[45] Feb. 8, 1977

[54] TERTIARY AMINES AS CATALYSTS IN POLYURETHANE MANUFACTURE

[75] Inventor: Arthur Ibbotson, Manchester, England

[73] Assignee: Imperial Chemical Industries Limited, London, England

[22] Filed: Jan. 8, 1975

[21] Appl. No.: 539,404

Related U.S. Application Data

[62] Division of Ser. No. 411,164, Oct. 30, 1973, abandoned.

[30] Foreign Application Priority Data

Nov. 1, 1972 United Kingdom ............ 50304/72

[52] U.S. Cl. .................... 260/2.5 AC; 260/75 NC; 260/77.5 AC; 260/552 R; 260/553 R; 260/561 A
[51] Int. Cl.² ....................................... C08G 18/18
[58] Field of Search ............ 260/2.5 AC, 77.5 AC, 260/75 NC

[56] References Cited

UNITED STATES PATENTS

| | | | |
|---|---|---|---|
| 3,073,787 | 1/1963 | Krakler | 260/2.5 AC |
| 3,234,153 | 2/1966 | Britain | 260/77.5 AC |
| 3,243,389 | 3/1966 | Moller et al. | 260/2.5 AC |
| 3,446,771 | 5/1969 | Matsubayashi et al. | 260/77.5 AC |

*Primary Examiner*—M. J. Welsh
*Attorney, Agent, or Firm*—Cushman, Darby & Cushman

[57] ABSTRACT

A tertiary amine having the general formula:

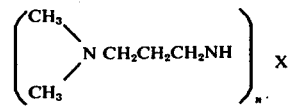

wherein X is the residue of an organic acid $X(OH)_n$, $n$ being the number of acidic groups present in the acid. The amines are useful as catalysts in the production of polyurethanes.

1 Claim, No Drawings

TERTIARY AMINES AS CATALYSTS IN POLYURETHANE MANUFACTURE

This is a division of application Ser. No. 411,164 filed Oct. 30, 1973 and now abandoned.

This invention relates to tertiary amines which are of value as catalysts for the reaction of isocyanates with active hydrogen compounds.

According to the invention there are provided tertiary amines having the general formula:

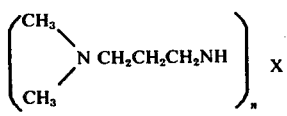

wherein X is the residue of an organic acid $X(OH)_n$, $n$ being the number of acidic groups present in the acid.

Examples of organic acid residues which may be represented by X when $n$ is 1 include groups of the formulae RCO- and RCS- wherein R represents hydrogen, an optionally substituted alkyl, cycloalkyl, aryl, aralkyl or heterocyclic radical or a group of the formula $-NR^1R^2$ in which $R^1$ and $R^2$ each independently represents hydrogen or an optionally substituted alkyl, cycloalkyl, aryl, aralkyl or heterocyclic radical.

Examples of organic acid residues which may be represented by X when $n$ is 2 include groups of the formulae -CO-, -CS- and -COQCO- wherein Q represents an optionally substituted divalent aliphatic, cycloaliphatic, aromatic, araliphatic or heterocyclic radical.

Examples of tertiary amines of the invention include N-(3-dimethylaminopropyl)formamide, N,N'-bis(3-dimethylaminopropyl) urea and N-(3-dimethylaminopropyl)-N'-phenylthiourea.

The tertiary amines of the invention may be prepared by reacting 3-dimethylaminopropylamine with an organic acid $X(OH)_n$ or an acylating agent derived therefrom. Suitable acylating agents include acid chlorides, acid anhydrides (including isocyanates and isothiocyanates) and lower alkyl esters of the said acids. Examples of suitable organic acids include formic, furoic, benzoic, adipic, citric, tartaric and carbonic acids as well as various carbamic and thiocarbamic acids.

The tertiary amines of the invention are useful organic bases and may be employed as catalysts for various reactions. In particular they are useful as catalysts for the reaction of organic isocyanates with active hydrogen compounds. More especially they are useful as catalysts for the production of polyurethanes by reacting organic polyisocyanates with organic polyols. A valuable characteristic of the tertiary amines of the invention is their low odour level compared with many other tertiary amines.

The starting materials to be used in the manufacture of polyurethanes, when the tertiary amines of the invention are employed as catalysts, have been fully described in the prior art.

Organic polyisocyanates which may be used include all those polyisocyanates that have already been proposed for use in the manufacture of polyurethanes. Preferably the polyisocyanate is a liquid at normal room temperatures. Of particular importance are the commercially available grades of tolylene diisocyanate and its isomer mixtures which may be in substantially pure, crude or polymeric forms. Also of importance are the so-called crude diphenylmethane diisocyanate compositions, particularly those containing from 30% to 90%, preferably from 40% to 80%, by weight of diphenylmethane diisocyanates, the remainder being largely polymethylene polyphenyl polyisocyanates of functionality greater than two. Such compositions may be obtained by the phosgenation of crude diaminodiphenylmethane as has been fully described in the prior art.

Examples of suitable organic polyols for use in making the polyurethanes include polyether polyols prepared by the reaction of one or more alkylene oxides with a compound containing a plurality of active hydrogen atoms. Suitable alkylene oxides include ethylene oxide, epichlorohydrin, 1,2-propylene oxide, 1,2-butylene oxide, 2,3-butylene oxide and styrene oxide. Mixtures of two or more oxides may be used if desired, for example mixtures of ethylene and propylene oxides, or, as a further variant, the active hydrogen-containing compound may be reacted with two or more alkylene oxides in successive stages, for example using propylene oxide in the first stage and ethylene oxide in the second or, conversely, ethylene oxide in the first stage and propylene oxide in the second. Compounds containing a plurality of active hydrogen atoms with which the alkylene oxides may be reacted include water, ammonia, hydrazine, cyanuric acid, phosphorous, phosphoric or phosphonic acids, polyhydroxy compounds, for example ethylene glycol, propylene glycol, diethylene glycol, glycerol, trimethylolpropane, triethanolamine, pentaerythritol, sorbitol, sucrose, phenolformaldehyde reaction products, resorcinol and phloroglucinol, aminoalcohols, for example monoethanolamine and diethanolamine, polyamines, for example ethylene diamine, hexamethylene diamine, tolylene diamines and diaminodiphenylmethanes and polycarboxylic acids, for example adipic acid, terephthalic acid and trimesic acid. The conditions for the reaction between the alkylene oxide and the active hydrogen containing compound may be those fully described in the prior art using, for example, basic catalysts such as potassium hydroxide or acidic catalysts such as boron trifluoride. The reaction products may have molecular weights of up to 10,000 according to the amount of alkylene oxide reacted with the active hydrogen-containing compound. Other suitable polyols are polyesters which may be made, for example, from polycarboxylic acids and polyhydric alcohols. Suitable polycarboxylic acids include succinic, glutaric, adipic, sebacic, phthalic, isophthalic, terephthalic and trimesic acids. Mixtures of acids may be used. Examples of polyhydric alcohols include ethylene glycol, propylene glycol, tetramethylene glycol, diethylene glycol, decamethylene glycol, glycerol, trimethylolpropane and pentaerythritol. The polyesters may contain amide groups introduced by including a proportion of diamine or aminoalcohol in the polyester-forming reaction mixture. Suitable diamines and amino-alcohols include ethylene diamine, hexamethylene diamine, tolylene diamines and ethanolamines. The polyesters suitably have molecular weights between 300 and 6000. The polyols may be selected in known manner so that the polyurethane has a flexible, rigid or semi-rigid structure.

By using the tertiary amines of the invention as catalysts, polyurethanes may be prepared in known manner in the form of rigid plastics materials, foamed or unfoamed elastomers, fibres, coating or adhesives but the amines are particularly useful as catalysts in the preparation of polyurethane foams.

In the preparation of foams, the reaction mixture also contains a blowing agent. Suitable blowing agents include water which reacts with the organic polyisocyanate to form carbon dioxide and inert low boiling materials, such as trichlorofluoromethane, which vaporise under the influence of the exothermic reaction. The amount of blowing agent is selected in known manner to provide foams of the desired density.

In addition to one or more tertiary amines of the invention, the foam-forming reaction mixture may contain one or more other catalysts for example other tertiary amines and organic tin compounds such as stannous octoate and dibutyltin dilaurate. Suitable amounts of tertiary amine to be employed as catalyst are usually in the range of from 0.1% to 5.0% based on the weight of organic polyol.

The foam-forming reaction mixture may also contain other conventional ingredients of such reaction mixtures. Thus, they may contain surfactants, for example siloxane-oxyalkylene copolymers, flame-retardants, for example tris chloropropyl phosphate, pigments, fillers and low molecular weight cross-linking agents such as ethylene glycol, glycerol and phenylene diamines.

The ingredients of the foam formulation may be brought together under any of the foam-forming conditions that have been described in the prior art relating to polyurethane foams. Thus, a one-shot foaming procedure may be employed in which foaming and polyurethane formation are brought about in a single operation, or any of the known prepolymer and quasi-prepolymer procedures may be used.

The invention is illustrated but not limited by the following Examples.

EXAMPLE 1

3-Dimethylaminopropylamine (26 g., 0.25 mole) was added dropwise during 30 minutes to a solution of phenyl isothiocyanate (33.75 g, 0.25 mole) in dry 80/100 petroleum ether (50 ml.). After cooling, the solution was filtered and the white crystalline solid so isolated crystallised from ethyl acetate. After drying for 8 hours in vacuo the yield was 30 g. (50% of theory) and the melting point 99° C. Both the infra-red and NMR spectra were consistent with the structure of N-phenyl-N'-(3-dimethylaminopropyl) thiourea.

EXAMPLE 2

3-dimethylaminopropylamine (26 g. 0.25 mole) was added dropwise over 30 minutes to a solution of cyclohexyl isocyanate (31.2 g., 0.25 mole) in dry 80/100 petroleum ether (50 ml.). The reaction was exothermic, the solution being at reflux during most of the addition time. After cooling, the solution was filtered to remove the solid reaction product precipitated on mixing the reactants. After washing with petroleum ether (2 × 75 ml.), the white crystalline solid was crystallised from ethyl acetate and dried in vacuo for 8 hours. The yield was 30 g. (55% of theory) m.p. 76° C. The infra-red and NMR spectra were consistent with the structure of N-cyclohexyl-N'-(3-dimethylaminopropyl) urea.

EXAMPLE 3

Ethylene carbonate (44 g., 0.5 mole) and 3-dimethylaminopropylamine (204 g., 2.0 mole) were heated at reflux (ca 140° C for 17 hours. Vacuum (15 mm Hg) was applied to remove unreacted amine to leave a 90% yield of a pale brown oily liquid of low smell. The infra-red and NMR spectra were consistent with the structure of N,N'-bis(3-dimethylaminopropyl)urea.

EXAMPLE 4

Formic acid (23 g., 0.5 mole), dimethylaminopropylamine (51 g., 0.5 mole) and toluene (50 ml) were azeotroped together with continual removal of water using a Dean and Stark separator until no more water was formed. Toluene was distilled off and the pale yellow residue distilled in vacuo. The colourless liquid product of low smell (N-(3-dimethylaminopropyl)formamide) was obtained in a yield of 59% of theory, b.p. 140° C/15 mm Hg.

EXAMPLE 5

A sample of oxypropylated glycerol of molecular weight approx. 411 (55.1 g) was mixed with 80/20 2,4-/2,6-tolylene diisocyanate (34.8 g) and cyclohexanone (5 ml). The temperature of the mixture after 15 minutes was 72° C The experiment was repeated using each of the catalysts (0.225 g) described in Examples 1–4 as a solution in the 5 ml of cyclohexanone and the temperature after 15 minutes was recorded thus:

| Catalyst of Example | Temperature after 15 minutes (° C) |
|---|---|
| 1 | 108 |
| 2 | 98 |
| 3 | 134 |
| 4 | 133. |

EXAMPLE 6

200 g of a polyether of hydroxyl value 32 mg KOH/g made by reacting glycerol with propylene oxide, and then with ethylene oxide so that the ethylene oxide is 13% by weight of the total alkylene oxides used were blended with 121 g of crude diphenylmethane diisocyanate for 57 secs at 2,000 r.p.m. Then, over 3 secs, 0.32 g of stannous octoate were added followed by an activator solution containing 2.0 g of bis($\gamma$dimethylaminopropyl) urea in 7.0 g of water. After stirring for 10 secs at the same speed the mixture was poured into a 17.8 cm × 17.8 cm mould. The foam rose to 15 cm in 73 secs and after 15 minutes was virtually tack-free.

The foam had no large voids or holes at the base and had a density of 37.69 Kg/m$^3$, and a resilience of 48%.

The crude diphenylmethane diisocyanate used in this Example had an NCO content of 30.8% and contained approximately 55% of diphenylmethane diisocyanate isomers.

The above Example was repeated using 3.00 g of a triethylene diamine based catalyst having the trade name "Dabco WT" instead of bis($\gamma$-dimethylaminopropyl)urea.

The resulting foam had a cream time of 25 secs., rose to 15 cm in 117 secs., had large voids and holes at the base and had a density of 36 Kg/m$^3$ and a resilience of 30%. The resilience of this foam was thus much lower than that made with the assistance of bis($\gamma$-dimethylaminopropyl)urea.

EXAMPLE 7

A repeat of Example 6 was carried out using 2.00 g of 3-dimethylaminopropyl formamide instead of bis(γ-dimethylaminopropyl)urea as catalyst.

This foam had a cream time of 10 secs., rose to 17.8 cm in 100 secs., had no large voids or holes at the base and had a density of 38 Kg/m$^3$ and a resilience of 48%.

EXAMPLE 8

Oxypropylated glycerol of molecular weight 410 (136.5 g) was mixed with the catalyst of Example 4 (1.0 g), water (0.5 g), and a siloxane oxyalkylene block copolymer surfactant (ε5340, 1.0 g) 150 g of crude diphenylmethane diisocyanate (as used in Example 6) were added and the mixture was stirred.

When it became warm it was poured into a metal mould where it slowly expanded to give a very hard fine tough rigid foam, suitable for reinforcement purposes.

I claim:
1. A method for the manufacture of polyurethane which comprises reacting an organic polyisocyanate with an organic polyol in the presence of a catalytically effective amount of
   N,N'-Bis(3-dimethylaminopropylamino)urea.

* * * * *